United States Patent
Poulter et al.

(10) Patent No.: US 7,736,881 B2
(45) Date of Patent: Jun. 15, 2010

(54) ANTIBACTERIAL AND HERBICIDAL COMPOUNDS AND SYSTEM FOR SCREENING THE SAME

(75) Inventors: C. Dale Poulter, Salt Lake City, UT (US); Frederick Hahn, Paia, HI (US); Rita Cornish, Salt Lake City, UT (US); Charles Testa, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 1677 days.

(21) Appl. No.: 10/399,129

(22) PCT Filed: Oct. 13, 2001

(86) PCT No.: PCT/US01/32143

§ 371 (c)(1),
(2), (4) Date: Apr. 11, 2003

(87) PCT Pub. No.: WO02/31120

PCT Pub. Date: Apr. 18, 2002

(65) Prior Publication Data

US 2004/0219656 A1    Nov. 4, 2004

Related U.S. Application Data

(60) Provisional application No. 60/240,253, filed on Oct. 13, 2000.

(51) Int. Cl.
*C12N 1/21* (2006.01)

(52) U.S. Cl. .............................. 435/252.3; 435/252.33; 435/243; 435/235.1; 536/23.2

(58) Field of Classification Search .............. 435/252.3, 435/252.33, 243, 235.1; 536/23.2
See application file for complete search history.

(56) References Cited

FOREIGN PATENT DOCUMENTS

| EP | 1260590 | 11/2002 |
|---|---|---|
| WO | WO 00/44912 | 8/2000 |
| WO | 01/11055 A1 | 2/2001 |
| WO | WO 01/64943 | 9/2001 |

OTHER PUBLICATIONS

Takagi et al., J. bacteriology 182 4153-4157 (Aug. 2000).*
Poteete, Anthony R. and Anita C. Fenton; "Genetic Requirements of Phage λ Red-Mediated Gene Replacement in *Escherichia coli* K-12;" Journal of Bacteriology, vol. 182, No. 8, Apr. 2000, p. 2336-2340.

Testa, Charles A. et. al; "The Sorbitol Phospotransferase System is Responsible for Transport of 2-C-Methyl-D-Erythritol into *Salmonella enterica* Serovar Typhimurium;" Journal of Bacteriology, vol. 186, No. 2, Jan. 2004, p. 473-480.
Hughes, Kelly T. and John R. Roth; "Transitory cis Complementation: A Method for Providing Transportation Functions to Defective Transposons;" The Genetics Society of America, 1998, p. 9-12.
Cane, David E., et al., "Molecular Cloning, Expression and Characterization of the First Three Genes in the Mevalonate-Independent Isoprenoid Pathway in *Streptomyces coelicolor*," Bioorganic & Medicinal Chemistry, 9, Jun. 2001, 1467-77.
Harker, M., et al. "Expression of Prokaryotic 1-deoxy-D-xyulose-5-phosphatases in *Escherichia coli* Increases Caralenoid and Ubiquinone Biosynthesis," FEBS Letters, 448, 115-119, (1999).
Jomaa, Hassan, et al, "Inhibitors of the Nonmevalonate Pathway of Isoprenoid Biosynthesis as Antimalarial Drugs," Science vol. 285, Sep. 3, 1999, 1573-1576.
Kim, Seon-Won, et al., "Metabolic Engineering of the Nonmevalonate Isopentenyl Diphosphate Synthesis Pathway in *Escherichia coli* Enhances Lycopene Production, " Biotechnology and Bioengineering, vol. 72, No. 4, Feb. 20, 2001, 408-415.
Lichtenthaler, H.K., "Sterols and Isoprenoids," BioChem Soc Trans, Dec. 2000, 28(b) 785-789.
Matthews, P.D., et al., "Metabolic Engineering of Carotenoid Accumulation in *Escherichia coli* by Modulation of the Isoprenoid Precursor Pool with Expression of Deoxyxylulose Phospate Synthase," Appl. Microbiol Biotechnol Apr. 2000, 53, 396-400.
Takahashi, Shunji, et al., "A 1-deoxy-D-xylulose 5-phosphate Reductoisomerase Catalyzing the Formation of 2-C-Methyl-D-Erythritol 4-Phosphate in an Alternative Nonmevalonate Pathway for Terpenoid Biosynthesis," Proc. Natl. Acad. Sci. USA, vol. 95, pp. 9879-9884, Aug. 1998.

* cited by examiner

*Primary Examiner*—Chih-Min Kam
(74) *Attorney, Agent, or Firm*—Knobbe Martens Olson & Bear LLP (57) ABSTRACT

A transgenic bacterial host cell that can be used as a screen for novel antibiotics and herbicides is provided. The genome of the transgenic bacterial host cell comprises disruptions in a first endogenous gene in the MEP pathway) and a transgene that functionally replaces the disrupted first gene. In other embodiments, the genome comprises a disruption in a first endogenous gene in the MEP pathway and a second endogenous gene which is located downstream of the first gene in the MEP pathway. A transgene that functionally replaces the disrupted downstream gene is cloned into the host cell. A mini operon containing the essential genes for the MVA pathway may also be cloned into the host cell. The transgenic host cell may be used in a method for screening compounds for antibiotic and herbicidal properties. The agents determined by the screening method may be used to kill bacteria or plants.

22 Claims, 2 Drawing Sheets

ANTIBACTERIAL AND HERBICIDAL COMPOUNDS AND SYSTEM FOR SCREENING THE SAME

1. RELATED APPLICATIONS

This application is a 371 of PCT/US01/32143, filed Oct. 13, 2001, and this application is related to and claims the benefit of U.S. Provisional Application No. 60/240,253 of C. Dale Poulter, filed Oct. 13, 2000 and entitled "A Screening Novel Antibacterial and Herbicidal Compounds", which is incorporated herein by this reference.

2. FIELD OF THE INVENTION

The present invention relates to antibacterial and herbicidal agents and systems and methods of screening for antibacterial and herbicidal agents. More specifically, the invention relates to antibacterial and herbicidal agents that interfere with the methylerythritol phosphate biosynthetic pathway for essential isoprenoid compounds and methods and systems for screening the same.

3. TECHNICAL BACKGROUND

When penicillin first became widely available it was a medical miracle. With penicillin, doctors were able to treat disease that was previously untreatable and often lethal. Soon, drug companies were mass-producing penicillin and doctors were giving it to patients frequently.

However, shortly after the start of widespread use of penicillin, bacteria began to appear that were resistant to the antibiotic. The first microbe to become resistant to penicillin was *Staphylococcus aureaus*. This bacterium is generally part of the harmless resident flora of the human body. However, it can also cause illness such as pneumonia.

Other bacteria began to show resistance to penicillin, and new antibiotics were discovered and introduced. With almost every introduction of a new antibiotic, bacteria have evolved a mechanism to resist the drug. Thus, bacteria have been found that are resistant to methicillin, oxacillin, chloramphenicol, neomycin, terramycin, tetracycline, and cephalosporins. Many bacteria are resistant to a number of types of antibiotics. Moreover, resistant bacteria can transfer the resistance gene to other bacteria—even bacteria of dissimilar species.

Despite the development of bacterial resistance to antibiotics, researchers have been able to discover new agents to battle the bugs. However, many of these new agents can also be toxic to humans. Moreover, the new agents may kill most of the resident microflora of the gastrointestinal tract, making the patient more susceptible to the invasion of disease causing bacteria.

Vancomycin has been used as the drug of last resort in treating multiple-resistant bacterial strains. However, bacterial strains have been discovered that resist vancomycin, and many medical experts fear that we will be without weapons to fight resistant bacteria.

Similar to the problems facing the treatment of bacterial disease are those associated with herbicidal agents. Herbicidal agents have been used by farmers, gardeners, and others for many years to combat undesirable plants and to increase crop yields. However, as with antibiotics, some plants have developed resistance to these compounds. Additionally, recent environmental regulations have caused some of the most effective herbicides to be discontinued because of potential harm to the environment and humans. Thus, there is a need to provide new herbicidal compounds that are less damaging to the environment and yet effective at killing undesirable plants.

One potential target for finding compounds that are effective antibacterial and/or herbicidal agents is the pathways for the synthesis of isoprenoid compounds. Isoprenoid compounds form a large ubiquitous class of natural products consisting of over 30,000 individual members. They fulfill a wide variety of cellular functions—such as components of cell membranes (sterols), electron transport (ubiquinones), signal transduction (prenylated proteins), photosynthetic pigments (chlorophylls), and cell wall biosynthesis (dolichols)—essential for viability.

Until recently, all isoprenoid compounds were thought to be synthesized from acetyl-CoA by the widely accepted mevalonate (MVA) pathway found in eukaryotes and archaebacteria. Work stimulated by labeling patterns in bacterial hopanoids and ubiquinones inconsistent with their biosynthesis by the MVA pathway led to the discovery of a new independent route to these molecules in many bacteria, green algae, and plants. In the newly discovered pathway, the five carbon atoms in the basic isoprenoid unit are derived from pyruvate and D-glyceraldehyde 3-phosphate (GAP). Pyruvate and GAP are condensed to give 1-deoxy-D-xylulose 5-phosphate (DXP).

In addition to serving as a precursor for the biosynthesis of thiamine and pyridoxol, DXP undergoes rearrangement and reduction to form 2-methylerythritol 4-phosphate (MEP), the first committed intermediate in the MEP pathway for biosynthesis of isoprenoids. MEP is then condensed with CMP to form a cytidine derivative, followed by phosphorylation of the C2 hydroxyl group and elimination of CMP to form a 2,4-cyclic diphosphate. The remaining steps to the fundamental five-carbon isoprenoid building blocks, isopentenyl diphosphate (IPP) and dimethylallyl diphosphate (DMAPP), have not been established. For most organisms reported to date, the enzymes in the MEP pathway are encoded by essential single copy genes. The exception is a *Streptomyces* gram-positive strain, which contains both the MEP and MVA pathways.

DXP synthase (DXPase) lies just before the branch point to the B vitamins and isoprenoids. Genes encoding the enzyme have been cloned from a number of species, including *E. coli*, *Streptomyces* sp. strain CL190, *Mentha x piperiia*, and *Capsicum annuum*. Disruption of the *E. coli* dxs gene is lethal. DXPase catalyzes the decarboxylation of pyruvate and the subsequent condensation of the thiamine bound two-carbon intermediate with GAP in a reaction similar to those catalyzed by transketolases. Interestingly, DXPases contain regions with strong homology to the $E_1$ subunit of pyruvate dehydrogenases and to transketolases. Although recombinant forms of the enzyme can use either GAP or D-glyceraldehyde as co-substrates with pyruvate, the phosphorylated form of the deoxy-sugar appears to be the normal intermediate in the pathway.

In light of the foregoing it would be a significant advancement in the art to provide a new method for screening for antibacterial and herbicidal agents. It would be a further advancement if the method produced compounds that were not toxic to humans and had decreased effect on the environment. An additional advancement would be to provide compounds that were effective antibiotics and herbicides. It would also be a significant advancement if an organism could be engineered for use in screening agents for activity against a large number of plants and bacteria. It would be a further advancement if the method could exploit the MEP pathway which is present in plants and eubacteria. Such organisms, compounds, and methods are disclosed and claimed herein.

4. BRIEF SUMMARY OF THE INVENTION

The present invention provides a transgenic bacterial host cell which can be used to screen for novel antibacterial and herbicidal agents. Such a transgenic bacterial host cell may have a genome with a disruption in a first gene in the endogenous methylerythritol phosphate (MEP) pathway. The genome may also contain a disruption in the second gene downstream from the first disrupted gene in the endogenous MEP pathway. Such disruptions may be an insertion or deletion that renders the endogenous gene functionally impaired. By functionally impaired, it is meant that the gene functions at a level below the normal wild-type function of the gene including non-functioning. The endogenous disrupted gene may be the DXP gene in the MEP pathway. However, other genes in the MEP pathway may be disrupted.

Most bacteria with a disruption in the MEP pathway are inviable. Thus, to culture such bacteria the disruption in the MEP pathway must be relieved. Such relief may be obtained by providing a chemical supplement that bi-passes the disrupted gene in the pathway.

When the bacterial host cell has a disruption in only the first gene in the MEP pathway, the genome of the transgenic bacterial host cell may have a cloned copy of a transgene that functionally replaces the first gene. When the bacterial host cell has a disruption in a first and second gene in the MEP pathway, the genome of the transgenic bacterial host may contain a cloned copy of a transgene that functionally replaces the disrupted second gene. The transgene may be from the same species of the transgenic bacterial host or from another species allowing a test agent to be screened for specific activity against a particular organism. The genome of the transgenic bacterial host cell may also contain a transgenic mevalonic acid (MVA) mini operon. The MVA operon provides an alternate pathway to vital isoprenoid compounds.

Common laboratory bacterial strains may be used for the transgenic bacterial host. Such common bacterial strains may be *E. coli* or *S. Typhimurium*. *E. coli* and *S. Typrimurium* are easy to culture, readily available, and do not pose a significant health threat to those in the laboratory. It will be appreciated that other bacterial strains may be used as the host cell notwithstanding their easy of culture, availability, and virulence.

The invention also provides a method of screening, novel antibacterial and herbicidal agents. The method can include the step of obtaining a transgenic bacterial host cell. The transgenic bacterial host cell has a genome as described above with a disruption in a first or a first and second gene in the MEP pathway and a cloned copy of a transgene that functionally replaces the disrupted first or second gene.

The transgenic bacterial host cell is cultured in a test culture. The media of the test culture contains a chemical supplement to relieve the block in the first gene. The test culture is contacted with a test agent. A control culture of the transgenic bacterial host cell is also grown in media containing a chemical supplement to relieve the block in the first gene. The control culture is not contacted with the test agent.

After a period of time the growth of the transgenic bacterial host cells in the test and the control cultures is observed and compared. When an agent renders the transgenic bacterial host cell inviable as compared to the control culture, then the test agent is a potential antibacterial or herbicidal agent.

When the transgenic bacterial host cell also comprises a MVA mini operon, the screening method may contain an additional control culture that pinpoints the mode of action of the test agent to the MEP pathway. The screening method thus includes the step of growing the test culture on media that contains a chemical supplement to relieve the block of the first disrupted gene in the MEP pathway. A control culture is grown in media containing MVA. Both the control culture and the test culture are contacted with a test agent. After a period of time the test culture and the control culture are observed and the growth of the transgenic host observed. A test agent that renders the test culture inviable and does not affect the viability of the control culture may be an effective antibacterial or herbicidal agent.

When the MVA mini operon is present in a bacterial host cell containing a disruption in the first gene in the MEP pathway and a cloned copy of a transgene that functionally replaces the first gene, the bacterial host cell will grow on minimal medium. The screening method may include contacting the transgenic host cell growing on minimal media with a test agent. A control can be made by contacting the transgenic host cell growing on media supplemented with MVA. When the test agent renders the transgenic host cell growing on minimal medial inviable and does not affect the viability of the culture on the media supplemented with MVA. The agent maybe an effective inhibitor of the cloned gene in the MVA pathway and thus an effective antibacterial or herbicidal agent.

The transgene that functionally replaces the first or second disrupted gene in the transgenic host cell may be from the same species as the host cell or from another species. When a transgene is used from a species other that the host cell, an agent may be tested for disrupting the gene of the specific organism from which the transgene originated. Thus, the test agent may be tested for its ability to kill the specific organism.

A method of selectively killing an organism such as bacterial cell or a plant is also provided. The method includes the step of contacting the organism with an antibacterial agent or herbicidal agent other than fosmidomycin which selectively inhibits the methylerythritol phosphate (MEP) pathway of the bacterial cell. The ability of the agent to selectively inhibit the MEP pathway of the organism cell can be determined by the screening method of the present invention. Thus, a transgenic bacterial host cell is obtained whose genome comprises a disruption of a first endogenous gene or a first and a second endogenous gene in the MEP pathway. The first gene may be a disruption in the endogenous DXP gene. The genome also contains a transgene obtained from an organism that functionally replaces the disrupted first or second gene. The transgenic host cell is then cultured on media containing a chemical supplement to relive the disruption of the first gene. A test culture is contacted with a test agent. The growth of the transgenic host cell in the presence of the test agent is compared to a control culture. An agent that inhibits the growth of the test culture indicates that the agent may inhibit the MEP pathway of the organism.

In order to determine if the mode of activity of the agent is the selective inhibition of the MEP pathway the bacterial host cell may also comprise a MVA mini operon. The activity of the test agent is determined by the step of growing the test culture on media that contains a chemical supplement to relieve the block of the first disrupted gene in the MEP pathway. A control culture is grown in media containing MVA. Both the control culture and the test culture are contacted with a test agent. After a period of time the test culture and the control culture are observed and the growth of the transgenic host observed. A test agent that renders the test culture inviable and does not affect the viability of the control culture may be an effective antibacterial or herbicidal agent.

5. SUMMARY OF THE DRAWINGS

A more particular description of the invention briefly described above will be rendered by reference to the appended drawings and graphs. These drawings and graphs only provide information concerning typical embodiments of the invention and are not therefore to be considered limiting of its scope.

6. DETAILED DESCRIPTION OF THE INVENTION

Isoprenoid compounds represent one of the largest and most diverse groups of natural products, with over 30,000 identified members to date. Poulter, C. D., & Rilling, H. C. In *Biosynthesis of Isoprenoid Compounds*; Porter, J. W., & Spurgeon, S. L., Eds., Wiley: New York, 1981; Vol. 1, pp. 161-224. These molecules perform a variety of important tasks in their host organisms, including serving as hormones in mammals, antioxidants in plants, and electron carriers during cellular respiration. Sacchetini, J. C., & Poulter, C. D. *Science* 277: 1788-1790 (1997). Isopentenyl diphosphate (IPP)[1] and dimethylallyl diphosphate (DMAPP) are the five-carbon building blocks used to construct more complicated isoprenoid structures.

Figure 1:
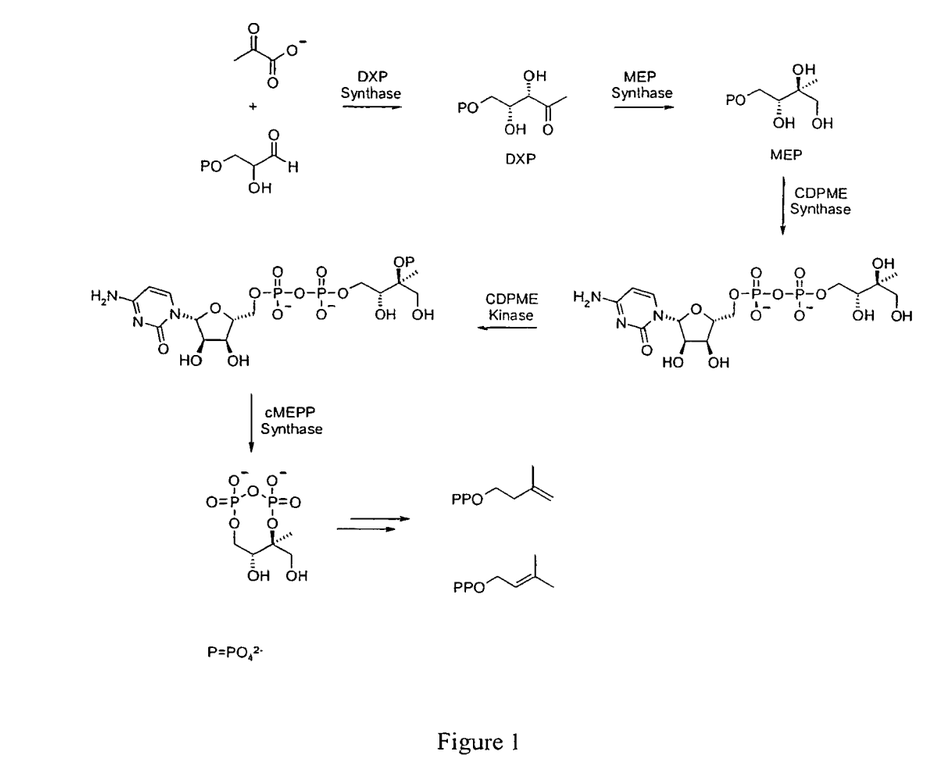
FIG. 1 is a schematic representation of the Methylerythritol Phosphate (MEP) Pathway.
Figure 2:
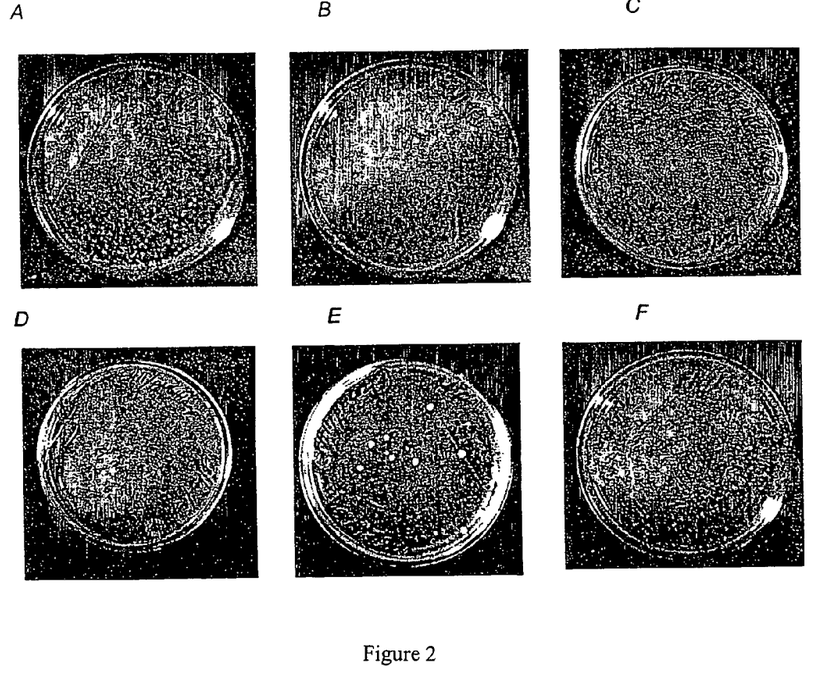
FIGS. 2A-2F are photographs showing the E. coli FH11 at 30° C. and 40° C.

Until recently, IPP and DMAPP were thought to originate from acetate via the mevalonate pathway. Bochar, D. A., et al. In *Comprehensive Natural Products Chemistry*; Barton, D., & Nakanishi, K., Eds., Elsevier: Oxford, 1999; Vol. 2, pp. 15-44. However, studies by Rohmer and Arigoni uncovered an alternate pathway that operates in plants, algae, and bacteria where IPP and DMAPP are derived from pyruvate and glyceraldehyde-3-phosphate. Flesch, G., & Rohmer, M., *Eur. J. Biochem.* 175: 405-411 (1988); Arigoni, D., et al., *Proc. Natl. Acad. Sci. U.S.A.*, 94: 10600-10605 (1997); Eisenreich, W., et al. *Chem. Biol.*, 5: R221-R233 (1998). Referring to FIG. 1, the two three-carbon precursors are joined in a thiamine diphosphate-mediated condensation catalyzed by 1-deoxy-D-xylulose-5-phosphate (DXP) synthase to give DXP. Lois, L. M., et al., *Proc. Natl. Acad. Sci. U.S.A.*, 95: 2105-2110 (1998). DXP is then rearranged and reduced by 2-C-methyl-D-erythritol-4-phosphate synthase (MEP synthase) (also called DXP reductoisomerase or DXP isomeroreductase) to form MEP. DXP, as well as its dephosphorylated counterpart deoxyxylulose, have also been identified as intermediates in the synthesis of vitamins $B_1$ and $B_6$. Begley, T. P., *Nat. Prod. Rep.*, 13: 177-185 (1996); Cane, D. E., et al., *J. Am. Chem. Soc.*, 121: 7722-7723 (1999). Thus, MEP is the first intermediate committed to IPP formation, and the name "methylerythritol phosphate pathway" has recently been suggested for this route (4th European Symposium on Plant Isoprenoids, Barcelona 1999). MEP is converted to 2-C-methyl-D-erythritol-2,4-cyclodiphosphate by the action of three successive enzymes. Rohdich, F., et al., *Proc. Natl. Acad. Sci. U.S.A.*, 96: 11758-11763 (1999); Kuzuyama, T., et al. *Tetrahedron Lett.*, 41: 703-706 (2000); Luttgen, H., et al., *Proc. Natl. Acad. Sci. U.S.A.*, 97: 1062-1067 (2000); Kuzuyama, T., et al. *Tetrahedron Lett.*, 41: 2925-2928 (2000); Herz, S., et al., *Proc. Natl. Acad. Sci. U.S.A.*, 97: 2426-2490 (2000); Takagi, M., et al. *Tetrahedron Lett.*, 41: 3395-3398 (2000).

Many bacteria, including the pathogens involved in human disease, many of which are becoming drug-resistant, rely on the recently discovered methylerythritol phosphate (MEP) pathway for the biosynthesis of essential isoprenoid compounds. Deletion of genes in the pathway or disruption on enzyme activity by inhibitors is lethal.

E. coli strains with disruptions in the genes encoding enzymes in MEP pathway are not viable. This is the only pathway for biosynthesis of essential isoprenoid compounds in E. coli and many other bacteria. The MEP pathway is also found in plant chloroplasts and in some species maybe required for biosynthesis of chlorophyll and photoprotective carotenoids. Gene disruptions in the MEP pathway can be complemented (1) chemically by supplementation with chemical intermediates in the pathway, (2) by plasmid encoded copies of the disrupted gene, and (3) by a mini-operon that encodes enzymes that synthesize isopentenyl diphosphate from mevalonate (MVA) and, thus, by-passes the MEP pathway.

Bacterial strains such as E. coli and S. typhimurium containing (1) a disruption in a first gene in the MEP pathway such as the wild-type gene for deoxyxylulose phosphate (DXP) and a disruption in a second gene downstream from the first gene in the MEP pathway, (2) a cloned-in copy of the downstream gene from the host or another organism, and (3) a MVA mini-operon are inviable when grown on rich or minimal media, but are viable when the medium contains a chemical supplement to relieve the block of the first gene or MVA. Addition of a compound to the medium that inhibits the plasmid-encoded downstream gene renders the strain inviable on media containing the chemical supplement but viable on MVA-supplemented media.

Likewise bacterial strains containing (1) a disruption in a first gene in the MEP pathway such as the wild-type gene for deoxylulose phosphate (DXP) (2) a cloned-in copy of the disrupted first gene from the host or another organism, and (3) a MVA mini-operon are inviable when grown on rich or minimal media, but are viable when the medium contains a chemical supplement to relieve the block of the first gene or MVA. Addition of a compound to the medium that inhibits the plasmid-encoded downstream gene renders the strain inviable on media containing the chemical supplement but viable on MVA-supplemented media.

These strains can be used to screen for inhibitors of these enzymes encoded by the downstream-disrupted genes by comparing viability in the presence and absence of chemical supplements relative to MVA. This is a highly selective method to screen for molecules that inhibit isoprenoid biosynthesis by targeting enzymes in the MEP pathway. The screen is selective for the cloned enzyme in an easily manipulated host, regardless of its source. This permits one to screen for inhibitors of enzymes from pathogens in a safe background and eliminates much of the cost and danger of discovering lead compounds effective against pathogens.

The MEP pathway is only found in eubacteria and plant chloroplasts. Other eukaryotic organisms and archaebacteria synthesize isoprenoid compounds by the MVA pathway and are not subject to the toxicity associated with inhibitors that are highly selective for enzymes in the MEP pathway.

The present invention provides a transgenic bacterial host cell which can be used to screen for novel antibacterial and herbicidal compounds. The genome of the transgenic bacterial host cell has disruption a in all endogenous gene of the MEP pathway. In certain embodiments, the gene is the dxs gene, the disruption of which blocks the DXP pathway of the bacterial host cell. An additional disruption of a second endogenous gene which is located downstream in the MEP pathway is also present. A gene which functionally replaces the disrupted downstream gene is cloned into the host cell from an organism such as a plant or bacterium. In certain embodiments, an MVA mini operon may be cloned into the host cell.

As used herein, the term "genome" refers to all of the genetic elements in a cell, including without limitation the genes located on chromosomes and extrachromosomal elements (such as plasmids).

It may be desirable that bacterial strains that can readily and safely be grown in the laboratory be used as the host cell. Such bacterial strains include *E. coli* and *S. typhimurium*.

The transgenic bacterial host cells may be used in a method of screening for antibacterial and herbicidal agents. The transgenic cells are cultured in media containing a chemical supplement that lifts the DXP block. The transgenic host cells are then contacted with a test agent. The cell growth of the test culture is compared to the growth in a control culture. Inviability of the host cell in the test culture compared to viability in the control culture indicates that the agent is effective of selectively killing the organism from which the transgene was obtained.

In certain embodiments in which the transgenic host cell contains a cloned-in MVA mini operon, the control culture may be a transgenic host cell grown in the presence of MVA, the chemical supplement that lifts the DXP block, and the test agent. When the transgenic hosts cells are inviable in the test culture and viable in the control culture, the test agent is an effective antibacterial or herbicidal agent against the organism.

The invention also provides methods of killing plants and bacteria with antibacterial and herbicidal agents determined by the methods of the present invention. Because these agents work via the MEP pathway, which is not found in eukaryolic cells other than in plant chloroplasts, these agents exhibit minimal toxicity and adverse effect on the environment. The method of selectively killing plants and bacteria uses an agent that selectively inhibits the MEP pathway of the plant or bacteria. The ability of an agent to selectively inhibit the MEP pathway of the organism can be determined by the screening methods of the invention. An agent that is determined to selectively inhibit the MEP pathway of an organism can be used to kill the organism by contacting the organism with the agent.

All publications, patents, patent applications, and commercial materials cited in this application, including those cited in the Appendix, are hereby incorporated by reference in their entirety.

In some embodiments, a transgenic bacterial host cell comprising a genome is disclosed. This genome may comprise a disruption of a first gene, wherein the first gene is an endogenous gene in the methylerythritol phosphate (MEP) pathway and a transgene that functionally replaces the disrupted first gene. In some embodiments, the genome may further comprise a transgenic mevalomc acid (MVA) mini operon. In other embodiments, the first gene is an endogenous dxs gene. In other embodiments the bacterial host cell is selected from the group consisting of *E. coli* and *S. Typhimurium*. In further embodiments, the transgene is from a species other than the bacterial host cell. Other embodiments have the transgene being from the same species as the bacterial host cell.

In other embodiments, a transgenic bacterial host cell comprising a genome is disclosed. The genome comprises a disruption of a first gene, wherein the first gene is an endogenous gene in the Methylerythritol phosphate (MEP) pathway, a disruption of a second gene, wherein the second gene is an endogenous gene downstream from the first gene in the MEP pathway, and a transgene that functionally replaces the disrupted second gene.

Embodiments also relate to a method of screening antibacterial and herbicidal agents for activity against an organism, the method comprising the step of obtaining a transgenic bacterial host cell whose genome comprises a disruption of a first gene, wherein the first gene is an endogenous gene in the Methylerythritol phosphate (MEP) pathway, a disruption of a second gene, wherein the second gene is an endogenous gene downstream from the first gene in the MEP pathway, and a transgene obtained from the organism that functionally replaces the disrupted second gene. The step of culturing a test culture of the transgenic bacterial host cell in media containing a chemical supplement to relieve the disruption of the first gene is also added. An additional step of contacting the transgenic bacterial host cell of the test culture with a test agent may be used. The step of culturing a control culture of the transgenic bacterial host cell in media containing a chemical supplement to relieve the disruption of the first gene may be used. Also, the step of comparing growth of the bacterial host cell contacted by the test agent to the growth of the bacterial host cell of the control culture, wherein the killing of the transgenic bacterial host cell of the test culture and the viability of the transgenic bacterial host cell of the control culture indicates that the test agent is an effective antibacterial or herbicidal agent against the organism may be used in the method.

Further embodiments may be designed in which the genome further comprises a transgenic mevalonic acid (MVA) mini operon, and the method further comprises growing a control culture of the bacterial host cell on media containing MVA, such that when an agent renders the bacterial host cell inviable in media containing a chemical supplement to relive the disruption of the first gene and viable on media containing MVA, the agent is an effective antibacterial or herbicidal agent against the organism.

In other embodiments, a method of screening antibacterial and herbicidal agents for activity against an organism is disclosed. The method comprises the step of obtaining a transgenic bacterial host cell whose genome comprises a disruption of a first gene, wherein the first gene is an endogenous gene in the Methylerythritol phosphate (MEP) pathway. The step of culturing a test culture of the transgenic bacterial host cell in media containing a chemical supplement to relieve the disruption of the first gene may also be added. The step of contacting the transgenic bacterial host cell of the test culture with a test agent may also be added. The step of culturing a control culture of the transgenic bacterial host cell in media containing a chemical supplement to relieve the disruption of the first gene. The step of comparing growth of the bacterial host cell contacted by the test agent to the growth of the bacterial host cell of the control culture may further be added. The killing of the transgenic bacterial host cell of the test culture and the viability of the transgenic bacterial host cell of the control culture indicates that the test agent is an effective antibacterial or herbicidal agent against the organism. In additional embodiments, the method is designed in which the genome further comprises a transgene obtained from the organism that functionally replaces the disrupted first gene, and wherein the test culture of the transgenic bacterial host cell is cultured in media containing a chemical supplement to activate the transgene and the control culture of the transgenic bacterial host cell is cultured in media containing a chemical supplement to activate the transgene.

4. EXAMPLES

The following examples are given to illustrate various embodiments which have been made with the present invention. It is to be understood that the following examples are not comprehensive or exhaustive of the many types of embodiments which can be prepared in accordance with the present invention.

Example 1

Construction of an *E. Coli* Strain Containing an Insert in the Deoxyxylulose Synthase Gene that Contains the Genes for Converting Mevalonic Acid to Isopentenyl Diphosphate An *E. coli* strain was constructed with a disruption in the gene for synthesis of deoxyxylulose (dxs), where the disruption consisted of an operon that coded for the yeast enzymes necessary to convert mevalonic acid (MVA) to isopentenyl diphosphate (IPP) under control of an arabinose promoter. This strain is capable of growing on media supplemented with methylerythritol (ME) by restoring isoprenoid metabolism through the methylerythritol phosphate (MEP) pathway or when supplemented with MVA through the MVA pathway.

Cloning *E. coli* dxs: The *E. coli* deoxyxylulose synthase gene (dxs) was PCR amplified using the following primers containing BamHI (bold) and KpnI (italics) restriction sites: 5'-GG*TACC*ATGAGTTTTGATATTGCCAAATACCCG-3' (SEQ ID NO: 1) (dxsPCR1) and 5'-GGATCCTTATGC-CAGCCAGCCAGGCC-3' (SEQ ID NO: 2). The PCR products were ligated directly into the pGEM-T Easy vector (Promega) to give pGEM-dxs. Upon restriction with BamHI and KpnI, fragment containing dxs was cloned into the BamHI/KpnI site of pBluescript SK+ (Stratagene) to give pBS-dxs.

Construction of pCAT53-3: A cassette containing the kanamycin resistance gene was obtained by restriction of plasmid pUC4K (Pharmacia) with SalI, cloning the fragments into the XhoI restriction site of pFCO1 to give pFCO1-kan containing the yeast genes for mevalonate kinase (erg8), mevalonate diphosphate decarboxylase (erg12) and phosphomevalonage kinase (erg19). The araC gene and the $P_{BAD}$ promotor were obtained by restriction of pBAD-gIII A (Invitrogen) with NsiI, filling in the ends with Klenow, and restriction with SacI. The gene cluster was cloned into pFCO1-kan that had been digested with SapI and filled in with Klenow and then restricted with SacI to give pCAT53-3.

Disruption of dxs with the mevalonate cluster: pCAT53-3 was restricted with PspOMI, the sticky ends were filled in with Klenow, the DNA was restricted with BsrBI, and the araC/$P_{BAD}$ DNA was cloned into HindIII restricted pBS-dxs using Chain Reaction Cloning to form pBS-dxs::pCAT53-3. *E. coli* strain JC7623 was transformed with plasmid pTP223. Poteete, A. R., et al., *Virology* 134: 161-167 (1984). To enhance homologous recombination. PBS-dxs::pCAT53-3 was linearized by restriction with SpeI and BsrBI and used to transform JC7623/pTP223 by electroporation. The transformants were plated on LB containing 40 µg/mL kanamycin and 50 µg/mL methylerythritol (ME). After two days at 37° C., the colonies were replicate plated on LB/kan/ME and LB/kan. Those colonies that grew on LB/kan/ME but not on LB/kan were plated on LB/kan/ME, LB/kan, and LB/kan/sodium mevalonate (5 mM)/0.02% arabinose (ara). Colonies that grew on LB/kan/ME and LB/kan/MVA/ara but not LB/kan were stored as glycerol stabs and frozen DMSO stocks.

Example 2

Construction of a *S. Typhimurium* Strain Containing an Insert in the Deoxyxylulose Synthase Gene that Contains the Genes for Converting Mevalonic Acid to Isopentenyl Diphosphate A *S. typhimurium* strain was constructed with an insertion in the gene that codes deoxyxylulose synthase (dxs). This insertion consisted of an operon, under the control of an arabinose promoter, which included the yeast genes necessary to convert mevalonic acid (MVA) to isopentenyl diphosphate (IPP). This strain is viable when supplemented with methylerythritol (ME) or MVA and arabinose, which restore in biosynthesis of IPP through the methylerythritol phosphate (MEP) pathway or MVA pathway respectively.

Cloning of *S. typhimurium* dxs: The *S. typhimurium* dxs gene was PCR amplified using primers sDXS1 and as DXS1. Primer sDXS1 is homologous to the upstream gene ispA while asDXS1 displayed homology to the region between dxs and the downstream gene yajO. The 2 kb PCR product was purified using QIAquick PCR purification kit (Qiagen) and then ligated into the vector pGEM-T (Promega) as directed by the manufacturer to give pRMC13. The ligation reactions were used to directly transform DH5α sub-cloning efficiency cells (Gibco-BRL) following the manufacturers instruction. The construct was verified by small scale plasmid purification using Qiagen's QIAprep spin miniprep kit followed by restriction digest with SacII.

Construction of pCAT53.3: A cassette containing the kanamycin resistance gene (Kan$^R$) was obtained by restriction of plasmid pUC4K (Pharmacia) with SalI. The Kan$^R$ fragment was then ligated into pFCO1, a plasmid which contains the yeast genes for mevalonate kinase (erg8), mevalonate diphosphate decarboxylase (erg12) and phosphomevalonate kinase (erg19), which had been digested with XhoI to produce pFCO1-kan. Hahn, F. M. et al. *J. Bacteriol* 183: 1-11 (2001) A cassette containing the gene araC and the $P_{BAD}$ promoter was obtained by first digesting pBAD-gIIIA (Invitrogen) with NsiI, then blunt ending by treatment Klenow, and finally restricting with SacI. This araC/$P_{BAD}$ cassette was directionally ligated into the SacI site and Klenow treated SapI site of pFCO1-kan resulting in plasmid pCAT53.3.

Construction of pRMC14: Plasmid pRMC13 was digested with EcoRV and Bsu361 to remove ~1000 bases from the middle of the dxs gene. Plasmid pCAT53.3 was digested with BstBI and PspOMI to liberate a fragment containing araC, PBAD, erg8, erg12, erg19 and Kan$^R$ (MevCluster) Fragments Bsu361-pRMC13-EcoRV and BsrBI-MevCluster-PspOMI were filled in with Klenow and directionally ligated using chain reaction cloning (CRC) with the primers crcKANDXS and crcDXSARA to form pRMC14. Pachuk, C. J. et al., *Gene* 243: 19-25 (2000). The CRC reactions were used to transform DH5a max-efficiency cells (Gibco-BRL) according to manufacturers instructions. The plasmid construct was verified by small scale plasmid purification using Qiagen's QIAprep spin miniprep kit followed by restriction digest with HindIII.

Disruption of dxs with the mevalonate cluster: Plasmid pRMC14 was electroporated into *S. typhimurium* strain TR6579 (obtained from John Roth, University of Utah) to produce strain RMC24. A medium scale plasmid purification was performed on this strain using Qiagen-tip 100 columns. Plasmid pRMC14, from this preparation, was digested with ApaI and SpeI to liberate a linear fragment containing the MevCluster, araC, P$_{BAD}$, and flanking regions of dxs homology. This linear fragment was electroporated into S. typhimurium strain TT22236 (LT2 harboring plasmid pTP223 obtained from John Roth, University of Utah) which contains a plasmid copy of the λ-Red genes to enhance homologous recombination. Poteete, A. R. & Fenton, A. C., Virology 134: 161-167 (1984). Recombinants were selected for on LB media containing Kan (50 µg/mL) and ME (50 µg/mL). A strain with insertion into dxs (RMC25) was isolated by replica plating to media with and without ME and screening for transformants viable only in the presence of ME. Insertion into dxs was verified by amplifying the regions of insertion (from inside the insert into the surrounding regions) using PCR with primers sISPA1 with asARAC1 and sKAN1 with asYAJO1 followed by sequencing. Strain RMC25 was then used as a donor to prepare a standard P22 HT105/λ int-201 lysate which was used to transduce dxs::pCAT53.3 into S. typhimurium strain LT2 resulting in strain RMC26 (S. typhimurium LT2 dxs::pCAT53.3). Achmieger, H., Mol. Gen. Genet. 110, 378-381 (1971). Again, this construct was verified by phenotype, as well as, PCR and sequencing.

TABLE 1

Primer Sequences

| Primer | Sequence |
|---|---|
| sDXS1 | 5'-CTGATAGAGGACGCCCGTCA-3' (SEQ ID NO: 3) |
| asDXS1 | 5'-CATAGCAGGAGCAAAGAGGG-3' (SEQ ID NO: 4) |
| crcKANDXS | 5'-TCGAGGTCGAGGGGGGGCCTGAG GGGCGAAAGTCGTAAA-3' (SEQ ID NO: 5) |
| crcDXSARA | 5'-CAATGAATCACGCAGGCGATCTC GCCGCAGCCGAACGACC-3' (SEQ ID NO: 6) |
| sISPA1 | 5'-CGTTAGACTTGGGCGTTGAG-3' (SEQ ID NO: 7) |
| asARAC1 | 5'-CTTTGAGCACCACCCGGAT-3' (SEQ ID NO: 8) |
| sKAN1 | 5'-GGCAGAGCATTACGCTGACT-3' (SEQ ID NO: 9) |
| asYAJO1 | 5'-AGTTAATGCCGCCCTCAAGG-3' (SEQ ID NO: 10) |

TABLE 2

Genotype of Strains of S. typhimurium LT2 and E. coli K-12

| Strain | Genotype | Plasmid | Ref./Source |
|---|---|---|---|
| LT2[a] | Wild type | | |
| LB5010[a] | MetA22 MetE551 trpD2 ilv-452-leu-pro- (leaky) hsdLT6 hsdSA29 hsdB-strA 120 galE- | | Bullas, L. R. & Ryu, J. J Bacteriol 156:471-474 (1983) |
| TT22236[a] | Wild type | TP223 | |
| RMC24[a] | MetA22 MetE551 trpD2 ilv-452-leu-pro- (leaky) hsdLT6 hsdSA29 hsdB-strA 120 galE- | pRMC14 | N/A |
| RMC25[a] | dxs520::MevOperon Δdxs520-1452 | | N/A |
| RMC26[a] | dxs520::MevOperon Δdxs520-1452 | | N/A |

TABLE 2-continued

Genotype of Strains of S. typhimurium LT2 and E. coli K-12

| Strain | Genotype | Plasmid | Ref./Source |
|---|---|---|---|
| DH5α[b] | F-F80dlacZDM15 D (lacZYA-argF)U169 deoR recA1 endA1 phoA hsdR17(rK-.mK-) supE44 I-thi-1 gyrA96 reIA1 | | Gibco-BRL |

[a]Strains of S. typhimurium LT2
[b]Strains of E. coli K-12

Example 3

Screen for Antimicrobial Agent Using Strain JC7623 dxs::pCAT53-3

Strain JC7623 dxs::pCAT53-3 was made chemically competent, transformed with pLME10 (R. capsulatus dxsB in pET11-A, manuscript in press) and grown in LB/kan/IPTG (kan$^r$ is in disruption and IPTG is for induction of plasmid derived dxs). A 5 µL portion of a 1,000 fold dilution was plated on plates as follows.

Plate a contained LB/kan/IPTG. Plate B contained LB/kan. Plate C contained LB/kan/MVA/arabinose. Plate D contained LB/kan/ME. Plate E contained LB/ka/IPTG/fosmidomycin. Plate F contained LB/kan/MVA/fosmidomycin. Plate G contained LB/kan/ME/fosmidomycin. The supplements in the media were present at the following concentrations: kan (40 mg/L), IPTG (1 mM), MVA (5 mM), arabinose (0.02%), ME (50 mg/L), fosmidomycin (~4 µg/mL).

After a period of 1 to 2.5 days the plates exhibited the following growth. Plate A slowed microcolonies after 1.5 days. Plate B showed microcolonies after 1.5 days. Plate C showed microcolonies after 1 day. Plate D showed colonies after 1 day. Plate E showed no growth after 2.5 days. Plate F showed microcolonies after 1 day. Plate G showed colonies after 1 day.

The growth rate of the plates was compared after 2.5 days. The growth on the plates D and G were equal. The growth on plates A and B were equal and less than the grown on plates D and G. The growth on plates C and F were equal and less than the growth on plates A and B. Plate E exhibited no growth.

These results demonstrate (1) that the disruption of dxs in the methylerytheilol phosphate (MEP) pathway for isoprenoid biosynthesis in E. coli can be complemented by a plasmid-encoded copy of the same enzyme from a different organism, (2) that a known inhibitor of the MEP pathway blocks growth, and (3) that growth is restored by supplementation with mevalonate (MVA) is provided along with the inhibitor. Thus, inhibitors of the MEP pathway block growth, and restriction of growth by MVA provides a positive control that pinpoints the mode of action of the inhibitor to the MEP pathway.

Example 4

Screen for Antimicrobial Agent Using Strain RMC25

Strain RMC25 was made electrocompetent, electroporated with pLME10 (R. capsulatus dxsB in pET11-A), and grown in LB/kan/amp/ME (kan$^r$ is in the DXS disruption and amp$^r$ is in pET11-A). A 5 μL portion of a 1,000 fold dilution was plated on plates A through G. Each plate contained supplements as follows. Plate A contained LB/kan/IPTG. Plate B contained LB/kan. Place C contained LB/kan/MVA/arabinose. Plate D contained LB/kan/ME. Plate E contained LB/kan/IPTG/fosmidomycin. Plate F contained LB/kan/MVA/fosmidomycin. Plate G contained LB/kan/ME/fosmidomycin. Concentrations for the supplements are as follows: kan (40 mg/L), IPTG (1 mM), MVA (5 mM), arabinose (0.02%), ME (50 mg/L), fosmidomycin (~4 μg/mL).

After 1 to 2.5 days growth was observed on the plates as follows. Plate A showed colonies after 1.5 days. Plate B showed microcolonies after 1.5 days. Plate C showed colonies after 1 day. Plate D showed colonies after 1 day. Plate E showed no growth after 2.5 days. Plate F showed colonies after 1 day. Plate G showed colonies after 1 day.

The growth rate of the plates was compared after 2.5 days. The growth on the plates D and G were equal. The growth on plates A was less than the grown on plates D and G. The growth on plates C and F were equal and less than the growth on plate A. The growth on plate B was less than the growth on plates C and F. Plate E exhibited no growth.

These results are demonstrate a constructed *S. typhimurium* strain can be used as a screen for drugs targeting the MEP pathway. The disrupted strain has the chromosomal copy of DXS disabled. This is a lethal condition when the strain is grown on LB media that does not contain mevalonate. The DXS disruption is complemented with a plasmid-encoded copy of one of the genes for DXS from *R. capsulatus*. The complemented strain grows on LB with a wt phenotype. When fosmidomycin, a compound that inhibits MEP synthase, is added to the media, growth is inhibited. Growth is restored when mevalonate is added to the media. Thus, the ability to screen for inhibition of a plasmid-encoded heterologous enzyme in the MEP pathway by monitoring growth of RMC25/pLME10 is demonstrated. Extensions of this procedure to other enzymes in the MEP pathway from other organisms are obvious and straightforward.

Example 5

Synthesis of IPP from MVA in *E. Coli*

The three yeast genes ERG8, ERG12, and ERG19 were isolated by PCR and were translationally coupled with overlapping start and stop codons in the synthetic operon contained within pFCO1. The PCR primers for all three yeast genes contained additional nucleotides for the ribosome-binding site AGGAGGAG (SEQ ID NO: 12) and the insertion of Gln-Glu-Glu-Phe (SEQ ID NO: 11) at the C-terminus of the encoded proteins to facilitate their purification using a monoclonal antibody column. The gene for mevalonate idnase, ERG12, served as the foundation for the construction of the operon. ERGS, the gene for phosphomevalonate kinase, was added upstream of ERG12, and ERG19, the gene for mevalonate diphosphate decarboxylase, was appended to the 3' end of ERG12. In order to ensure specific annealing to ERG12, the additional nucleotides corresponding to codons for the N-terminus of mevalonate diphosphate decarboxylase were altered during the design of primer FH0129 to direct the synthesis of the correct amino acids using codons as different as possible from wt ERG19. A cassette containing the coupled yeast genes was removed from pFCO1 and inserted into pNGH1-Amp to give pFCO2 in order to test the ability of the operon to complement the dxs::kan$^r$ disruption in FH11 grown on MVA.

Referring to FIG. 2, the cells of plate A were able to grow at 30° C. on LB/Kan medium. The cells of plate B were unable to grow at the nonpermissive temperature of 44° C. on LB/Kan medium, establishing that *E. coli* dxs is an essential gene. The cells of plate C were FH11 cells with *R. Capsulatus* OFR 2895 contained in pFMH39. These cells were able to grow at the nonpermissive temperature of 44° C. on LB/Kan/Amp medium establishing that *R. capsulatus* OFR 2895 encodes dxsB. As shown in plate D FH11/pNGH1-Amp cells containing the parent vector of pFMH39 and pFCO2 were unable to grow at 44° C. on LB/Kan/Amp medium. The cells of plate E were FH11/pFCo2 cells that were able to grow at 44° on LB/Kan/Amp medium supplemented with 2 mg/ml mevalonic acid establishing the ability of the synthetic operon contained within pFCO2 to synthesize IPP. The FH11 cells of plate F where able to grow at the nonpermissive temperature of 44° C. on LB/Kan medium containing about 0.3 mg/ml methrylerthritol. Thus, CFH11/pFCO2 transformants did not grow at the restrictive temperature of 44° C. unless MVA (50 mg/L) was added to the growth medium, establishing the ability of the synthetic operon to direct synthesis of IPP from MVA in *E. coli*.

The invention claimed is:

1. A transgenic bacterial host cell comprising a genome that comprises:

a disruption of a first gene that functionally impairs the first gene, wherein the first gene is an endogenous gene in the methylerythritol phosphate (MEP) pathway; and a transgene under control of an exogenous inducible promoter, wherein said transgene functionally replaces the disrupted first gene, wherein the transgene is either the same gene as the disrupted gene from the same organism, or the transgene encodes a functional equivalent of The disrupted gene from a different organism, wherein the transgenic bacterial host cell further comprises genes encoding phosphomevalonate kinase, mevalonate kinase, and mevalonate diphosphate decarboxylase.

2. The transgenic bacterial host cell of claim 1, wherein the first gene is an endogenous dxs gene.

3. A trausgenic bacterial host cell comprising a genome that composes:

a disruption of a first gene that functionally impairs the first gene, wherein the first gene is an endogenous gene in the methylerythritol phosphate (MEP) pathway, wherein the first gene is an endogenous dxs gene;

a transgene under control of an exogenous inducible promoter, wherein the transgene functionally replaces the disrupted first gene; and genes encoding phosphomevalonate kinase, mevalonate kinase, and mevalonate cliphosphate decarboxylase.

4. The trausgenic bacterial host cell of claim 3, wherein the bacterial host cell is selected from the group consisting of *E. coli* and *S. typhimurium*.

5. A transgenic bacterial host cell comprising a genome that comprises:

a disruption of a first gene that functionally impairs the first gene, wherein the first gene is an endogenous gene in the methylerythritol phosphate (MEP) pathway;

a disruption of a second gene that functionally impairs the second gene, wherein the second gene is an endogenous gene downstream from the first gene in the MEP pathway; and a transgene that functionally replaces the disrupted second gene, wherein the transgene is either the same gene as the disrupted gene from the same organism, or the transgene encodes a functional equivalent of the disrupted gene from a different organism, wherein the transgenic host cell farther comprises genes encoding phosphomevalonate kinase, mevalonate kinase, and mevalonate diphosphate decarboxylase.

6. The transgenic bacterial host cell of claim 5, wherein the first gene is an endogenous dxs gene.

7. The transgenic bacterial host cell of claim 6, wherein the bacterial host cell is selected from the group consisting of *E. coli* and *S. typhimurium*.

8. The transgenic host cell of claim 5, wherein the transgene is from a species other than the bacterial host cell.

9. The transgenic host cell of claim 5, wherein the transgene is from the same species as the bacterial host cell.

10. The transgenic host cell of claim 5, wherein the transgenic bacterial host cell is selected from the group consisting of *E. coli* and *S. typhimurium*.

11. A method of screening antibacterial and herbicidal agents for activity against an organism, the method comprising the steps of:

obtaining a transgenic bacterial host cell whose genome comprises a disruption of a first gene that functionally impairs the first gene, wherein the first gene is an endogenous gene in the Methylerythritol phosphate (MEP) pathway, a disruption of a second gene that functionally impairs the second gene, wherein the second gene is an endogenous gene downstream from the first gene in the MEP pathway, and a transgene that functionally replaces the disrupted first and/or second gene, wherein the transgene is either the same gene as the disrupted gene from the same organism, or the transgene encodes a functional equivalent of the disrupted gene from a different organism; providing a test culture and a control culture of the transgenic bacterial host cell;

complementing the disruption of the MEP pathway genes of the transgenic bacterial host cells of the test culture and the control culture by (a) contacting the transgenic bacterial host cell with a chemical supplement that bypasses the disrupted first and/or second gene in the MEP pathway, and/or (b) expressing the transgene in the transgenic bacterial host cell that functionally replaces the disrupted first and/or second gene in the MEP pathway;

contacting the transgenic bacterial host cell of the test culture with a test agent; and comparing growth of the transgenic bacterial host cell of the test culture to the growth of a bacterial host cell of the control culture, wherein the killing of the transgenic bacterial host cell of the test culture and the viability of the transgenic bacterial host cell of the control culture indicates that the test agent is an effective antibacterial or herbicidal agent against the organism.

12. The method of claim 11, wherein the bacterial host cell is selected from the group consisting of *E. coli* and *S. typhimurium*.

13. The method of claim 11, wherein the transgenic host cell further comprises genes encoding phosphomevalonate kinase, mevalonate kinase, and mevalonate diphosphate decarboxylase, wherein the test culture and control culture of the transgenic bacterial host cell are optionally contacted with mevalonic acid (MVA) to bypass the MEP pathway.

14. The method of claim 11, wherein the first gene is an endogenous dxs gene.

15. The method of claim 11, wherein the transgene is from a species other than the bacterial host cell.

16. The method of claim 11, wherein the transgene is from the same species as the bacterial host cell.

17. The method of claim 11, wherein the transgenic bacterial host cell is cultured under conditions to express the transgene.

18. A method of screening antibacterial and herbicidal agents for activity against an organism, the method comprising the steps of:

obtaining a transgenic bacterial host cell whose genome comprises a disruption of a first gene that functionally impairs the first gene, wherein the first gene is an endogenous gene in the Methylerythritol phosphate (MEP) pathway, and a transgene that functionally replaces the disrupted first gene, wherein the transgene is either the same gene as the disrupted gene from the same organism, or the transgene encodes a functional equivalent of the disrupted gene from a different organism;

complementing the disruption of the first gene of the transgenic bacterial host cells of the test culture and the control culture by (a) contacting the transgenic bacterial host cell with a chemical supplement that bypasses the disrupted first gene in the MEP pathway, and/ or (b) expressing the transgene in the transgenic bacterial host cell that functionally replaces the disrupted first gene in the MEP pathway;

contacting the transgenic bacterial host cell of the test culture with a test agent; and comparing growth of the bacterial host cell contacted by the test agent to the growth of the bacterial host cell of the control culture, wherein the killing of the transgenic bacterial host cell of the test culture and the viability of the transgenic bacterial host cell of the control culture indicates that the test agent is an effective antibacterial or herbicidal agent against the organism.

19. The method of claim 18, wherein the first gene is an endogenous dxs gene.

20. The method of claim 18, wherein the test culture of the transgenic bacterial host cell is cultured under conditions to express the transgene.

21. The method of claim 18, wherein the transgenic host cell further comprises genes encoding phosphomevalonate kinase, mevalonate kinase, and mevalonate diphosphate decarboxylase, and wherein the test culture and control culture of the transgenic bacterial host cell are optionally contacted with mevalonic acid (MVA) to bypass the MEP pathway, wherein when an agent renders the transgenic bacterial host cell inviable when the host cell is (a) contacted with a chemical supplement that bypasses the disrupted first gene in the MEP pathway, in the absence of MVA and/or (b) when the transgene in the transgenic bacterial host cell that bypasses the disrupted first gene in the MEP pathway is expressed in the absence of MVA, and wherein the transgenic host cell is viable when contacted with MVA, the agent is an effective antibacterial or herbicidal agent against the organism.

22. A method of screening antibacterial and herbicidal agents for activity against an organism, the method comprising the steps of:

obtaining a transgenic bacterial host cell whose genome comprises: (1) a disruption of a first gene that functionally impairs the first gene, wherein the first gene is an endogenous gene in the Methylerythritol phosphate (MEP) pathway, (2) a disruption of a second gene that functionally impairs the second gene, wherein the second gene is an endogenous gene downstream from the first gene in the MEP pathway, (3) a transgene that functionally replaces the disrupted first and second genes, wherein the each transgene is independently either the same gene as the disrupted gene from the same organism, or encodes a functional equivalent of the disrupted gene from a different organism, and (4) genes encoding phosphomevalonate kinase, mevalonate kinase, and mevalonate diphosphate decarboxylase;

providing a first and second test culture and a first and second control culture of the transgenic bacterial host cell;

complementing the disruption of the MEP pathway genes of the transgenic bacterial host cells of the test cultures and the control cultures, wherein the complementation comprises at least one of the following: (a) contacting the transgenic bacterial host cell with a chemical supplement that bypasses the disrupted second gene in the MEP pathway, (b) expressing the transgenes in the transgenic bacterial host cell that functionally replace the disrupted first and second genes in the MEP pathway, or (c) contacting the transgenic bacterial host cell with a chemical supplement that bypasses the disrupted first gene and expressing the transgene in the transgenic bacterial host cell that functionally replaces the second gene in the MEP pathway;

bypassing the MEP pathway in the first test culture and first control culture by contacting the first test culture and the first control culture with mevalonic acid;

contacting the transgenic bacterial host cell of the test cultures with a test agent; and comparing growth of the transgenic bacterial host cell of the test cultures to the growth of the transgenic bacterial host cell of the control cultures, wherein when first test culture is viable and the second test culture is inviable, the agent is an effective antibacterial or herbicidal agent against the organism.

* * * * *

SEQUENCE LISTING

```
<160> NUMBER OF SEQ ID NOS: 12

<210> SEQ ID NO 1
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 1
ggtaccatga gttttgatat tgccaaatac ccg                                33

<210> SEQ ID NO 2
<211> LENGTH: 26
<212> TYPE: DNA
<213> ORGANISM: Artificial sequence
<220> FEATURE:
```

```
<223> OTHER INFORMATION: Synthetic oligonucleotide

<400> SEQUENCE: 2
ggatccttat gccagccagc caggcc                                          26

<210> SEQ ID NO 3
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 3
ctgatagagg acgcccgtca                                                 20

<210> SEQ ID NO 4
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 4
catagcagga gcaaagaggg                                                 20

<210> SEQ ID NO 5
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 5
tcgaggtcga ggggggcct gagggcgaa agtcgtaaa                              39

<210> SEQ ID NO 6
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 6
caatgaatca cgcaggcgat ctcgccgcag ccgaacgacc                           40

<210> SEQ ID NO 7
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 7
cgttagactt gggcgttgag                                                 20

<210> SEQ ID NO 8
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 8
ctttgagcac cacccggat                                                  19
```

```
<210> SEQ ID NO 9
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 9
ggcagagcat tacgctgact                                              20

<210> SEQ ID NO 10
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 10
agttaatgcc gccctcaagg                                              20

<210> SEQ ID NO 11
<211> LENGTH: 4
<212> TYPE: PRT
<213> ORGANISM: Artificial Sequence
<220> FEATURE:
<223> OTHER INFORMATION: epitope tag

<400> SEQUENCE: 11

Gln Glu Glu Phe

<210> SEQ ID NO 12
<211> LENGTH: 8
<212> TYPE: DNA
<213> ORGANISM: Artificial Sequence
<220> FEATURE:
<223> OTHER INFORMATION: ribosome binding site

<400> SEQUENCE: 12 aggaggag                                                            8
```